(12) United States Patent
Fromentin (10) Patent No.: US 10,838,111 B2
(45) Date of Patent: Nov. 17, 2020

(54) OPTICAL MATERIAL COMPRISING A RED-SHIFTED BENZOTRIAZOLE UV ABSORBER

(71) Applicant: ESSILOR INTERNATIONAL, Charenton-le-Pont (FR)

(72) Inventor: Pierre Fromentin, Bangkok (TH)

(73) Assignee: Essilor International, Charenton-le-Pont (FR)

( * ) Notice: Subject to any disclaimer, the term of this patent is extended or adjusted under 35 U.S.C. 154(b) by 101 days.

(21) Appl. No.: 16/095,556

(22) PCT Filed: Apr. 21, 2017

(86) PCT No.: PCT/EP2017/059535
§ 371 (c)(1),
(2) Date: Oct. 22, 2018

(87) PCT Pub. No.: WO2017/182639
PCT Pub. Date: Oct. 26, 2017

(65) Prior Publication Data
US 2019/0107647 A1  Apr. 11, 2019

(30) Foreign Application Priority Data

Apr. 21, 2016 (EP) .................................. 16305469

(51) Int. Cl.
*G02B 1/04* (2006.01)
*C07D 249/20* (2006.01)
(Continued)

(52) U.S. Cl.
CPC ........... *G02B 1/041* (2013.01); *C07D 249/20* (2013.01); *C08G 18/52* (2013.01); *C08G 18/72* (2013.01);
(Continued)

(58) Field of Classification Search
CPC ...... G02B 1/041; C07D 249/20; C08G 18/52; C08G 18/72; C08L 69/00
(Continued)

(56) References Cited

U.S. PATENT DOCUMENTS 4,719,248 A  1/1988 Bambury et al.
7,803,359 B1  9/2010 Jinkerson et al.
(Continued)

FOREIGN PATENT DOCUMENTS

EP  2963457  1/1916
EP  0682082  11/1995
(Continued)

OTHER PUBLICATIONS

Belusa et al., "2-(2-Hydroxyphenyl benzotriazoles. I. Synthesis and their ultraviolet and infrared spectra," *Chem. Zvesti.*, 1974, 28(5):673-679.
(Continued)

*Primary Examiner* — James R Greece
(74) *Attorney, Agent, or Firm* — Norton Rose Fulbright US LLP (57) ABSTRACT

The present invention relates to an eyeglass lens comprising a substrate made of an optical material comprising a polymer matrix and at least one 2-(2-hydroxy-5-$R^1$-phenyl) benzotriazole, in which $R^1$ is a resonant group, the optical transmittance through a 2 mm thick layer of said optical material being lower than 1% for each light wavelength ranging from 280 to 405 nm. This eyeglass lens protects from phototoxic blue light and UV light.

15 Claims, 2 Drawing Sheets

— Seesorb 703 (VII)
-- Tinuvin Carboprotect
-- Compound (IV)
-- Compound (V)
-- Compound (VI)

(51) Int. Cl.
  *C08G 18/52* (2006.01)
  *C08G 18/72* (2006.01)
  *C08L 69/00* (2006.01)
  *C08G 75/08* (2006.01)
  *C08L 33/10* (2006.01)
  *C08L 75/04* (2006.01)

(52) U.S. Cl.
  CPC .............. *C08L 69/00* (2013.01); *C08G 75/08* (2013.01); *C08L 33/10* (2013.01); *C08L 75/04* (2013.01)

(58) Field of Classification Search
  USPC .................................................... 351/159.65
  See application file for complete search history.

(56) References Cited

U.S. PATENT DOCUMENTS

| | | |
|---|---|---|
| 2003/0236418 A1 | 12/2003 | Hong |
| 2010/0113641 A1 | 5/2010 | Laredo |
| 2011/0217544 A1* | 9/2011 | Young ................. B29C 37/0032 428/327 |
| 2015/0370094 A1 | 12/2015 | Hashimoto et al. |
| 2016/0215121 A1 | 7/2016 | Kousaka et al. |

FOREIGN PATENT DOCUMENTS

| | | |
|---|---|---|
| EP | 1085348 | 3/2001 |
| JP | 2005-343119 | 12/2005 |
| WO | WO 2015/072991 | 5/2015 |

OTHER PUBLICATIONS

International Search Report and Written Opinion issued in International Patent Application No. PCT/EP2017/059535, dated May 26, 2017.
Lagarrigue et al., "Absorption of sound by porous layers with embedded periodic arrays of resonant inclusions", *J. Acoust. Soc. Am.*, 134(6): 4670-4680, 2013.
Wikipedia. "Benzotriazole." Datasheet [online]. Retrieved from the Internet: <URL: https://en.wikipedia.org/wiki/Benzotriazole> pp. 1-4.

* cited by examiner

OPTICAL MATERIAL COMPRISING A RED-SHIFTED BENZOTRIAZOLE UV ABSORBER

CROSS-REFERENCE TO RELATED APPLICATIONS

This application is a national phase application under 35 U.S.C. § 371 of International Application No. PCT/EP2017/059535 filed 21 Apr. 2017, which claims priority to European Patent Application No. 16305469.5 filed 21 Apr. 2016. The entire contents of each of the above-referenced disclosures is specifically incorporated by reference herein without disclaimer.

The present invention relates to optical materials comprising compounds that absorb UV light and generally at least part of the blue light of the visible spectrum, and more particularly to ophthalmic lenses containing these materials. The present invention is also directed to methods of making these materials.

Light that is visible to humans extends over a light spectrum ranging from a 380 nanometers (nm) wavelength to a 780 nm wavelength approximately. The part of this spectrum, ranging from around 380 nm to around 500 nm, corresponds to a high-energy range, essentially blue light.

Many studies (see for example Kitchel E., "The effects of blue light on ocular health", Journal of Visual Impairment and Blindness Vol. 94, No. 6, 2000 or Glazer-Hockstein and al., Retina, Vol. 26, No. 1. pp. 1-4, 2006) suggest that part of the blue light has phototoxic effects on the human eye health, and especially on the retina. Ocular photobiology studies demonstrated that an excessively prolonged or intense exposure to blue light may induce severe ophthalmic diseases such as age-related macular degeneration (ARMD) or cataract. Thus, it is recommended to limit the exposure of the eyes to blue light potentially harmful, in particular as regards the wavelength band with an increased dangerousness (420-450 nm).

Eyeglasses are particularly suitable to offer protection against such potentially harmful blue light.

It is furthermore necessary to eliminate as much as possible the harmful influence of ultraviolet light (UV light) on the eye of a wearer of the lens. Ultraviolet (UV) light is the portion of the luminous spectrum below 380 nm and ranging up to 100 nm. The UV spectrum has many bands, especially UVA, UVB and UVC bands. Amongst those UV bands reaching the earth surface, the UVA band, ranging from 315 nm to 380 nm, and the UVB band, ranging from 280 nm to 315 nm, are particularly harmful to the retina.

It has already been suggested to cut at least partially UV light and/or the troublesome part of the blue light spectrum from 400 nm to 460 nm, by means of one or more filters inhibiting the light in a suitable wavelength range, through absorption or through reflection.

Optical filtering means such as UV absorbers are frequently incorporated in optical articles in order to reduce or prevent UV light from reaching the retina (in particular in ophthalmic lens materials), but also to protect the substrate material itself, thus preventing it from weathering and becoming brittle and/or yellow. The commonly used UV absorbers are benzotriazole and benzophenone derivatives.

The UV absorber can be incorporated into the finished product through different technologies at different locations, generally in a coating such as a hard coat, but also in the bulk substrate, for example by impregnation of the substrate, or by incorporation in a substrate precursor formulation.

UV-absorbing benzotriazoles have been widely used in contact lenses/intraocular lenses, but these compounds contain polymerizable groups to ensure reticulation of the UV absorber within the substrate during polymerization, which alters the benzotriazole molecule.

WO 2015/072991 discloses a family of copolymerizable 2-[2'-hydroxy-3'-$R^1$-5'-$OR^2$]-5-trifluoromethyl-2H-benzotriazoles, in which $R^1$ is a tertiary alkyl group and $R^2$ comprises an olefinic polymerizable group such as a methacrylate group that can be used as UV absorbing compounds that are effective in blocking UV and short-wavelength blue light. Due to the presence of a polymerizable group in their structure, these compounds are copolymerizable with other ingredients in ophthalmic device formulations and are used in implantable ophthalmic lenses such as intraocular lenses and contact lenses. The devices exhibit 1% light transmission cut-off wavelengths of 430-440 nm.

For an identical purpose, U.S. Pat. No. 7,803,359 discloses a family of 2-[2'-hydroxy-5'-$OR^9$]-5-$OR^1$-6-$OR^3$-2H-benzotriazole, in which $R^9$ is H, an alkyl group or an olefinic polymerizable group such as a methacrylate group, R1 and R3 independently represent H, an alkyl or a phenyl group. The devices exhibit 1% light transmission cut-off wavelengths of 410-425 nm.

US 2010/113641 discloses a family of copolymerizable 2-[2'-hydroxy-3'-$R^1$-5'-alkoxy]-2H-benzotriazoles, in which $R^1$ is a substituent comprising an acrylate group. They are used in implantable ophthalmic lenses and contact lenses as UV absorbers and provide 1% light transmission cut-off wavelengths of 410-430 nm.

EP 0682082 describes an UV- and infrared-ray absorbing polymer composition (copolyestercarbonate resin), which is used for windows or screens adjacent to windows of vehicles and buildings and selectively transmits visible light rays and screens out harmful ultraviolet rays and infrared rays. The composition comprises at least one organic UV-absorber that must not disturb visible radiation transmittance, selected from 2-(2'-hydroxy-5'-methylphenyl)-benzotriazole, 2-(2'-hydroxy-3',5'-di-t-butylphenyl)-5-chloro-benzotriazole, 2-(2'-hydroxy-3'-t-butyl-5'-methylphenyl)-5-chloro-benzotriazole, 2-(2'-hydroxy-3',5'-di-t-aminophenyl)-benzotriazole, 2-(2'-hydroxy-3',5'-di-t-butylphenyl)-benzotriazole, 2-(2'-hydroxy-5'-t-butylphenyl)-benzotriazole, 2-(2-hydroxy-5'-t-octylphenyl)-benzotriazole. The UV light blocking performances are not very good, as UV transmission of the final material is higher than 1%, except when 2-(2'-hydroxy-3'-t-butyl-5'-methylphenyl)-5-chlorobenzotriazole (commercialized under the trade name Seesorb® 703) is employed.

A few patent applications describe the incorporation of benzotriazole UV absorbers in an eyeglass lens substrate. WO 2015/046540 discloses plastic lens substrates having a high blue light protection factor (35% or more in the 380-500 nm range), containing 2-(2'-hydroxyphenyl)benzotriazoles having a group imparting a mesomeric effect on the benzotriazole ring. The benzotriazole compounds may be selected from 2-(2'-hydroxy-3'-t-butyl-5'-methylphenyl)-5-chloro-benzotriazole, 2-(2'-hydroxy-3'-t-butyl-5'-ethylphenyl)-5-chloro-benzotriazole, 2-(2'-hydroxy-3',5'-dimethylphenyl)-5-chloro-benzotriazole, 2-(2'-hydroxy-3',5'-diethylphenyl)-5-chloro-benzotriazole and 2-(2'-hydroxy-4'-R-phenyl)-5-chloro-benzotriazole in which R=methoxy, ethoxy, butoxy or octyloxy. Dimeric compounds with two 2-(2'-hydroxyphenyl)benzotriazole groups per molecule are also described WO 2014/133111 discloses an optical material comprising at least one UV absorber having a maximum absorption peak ranging from 350 nm to 370 nm, which is configured to restrict exposure of the eyes of a user to blue light with relatively short wavelengths, specifically in the 400 to 420 nm wavelength range. The benzotriazoles that can be used are 2-(2-hydroxy-3-t-butyl-5-methylphenyl)-chlorobenzotriazole (Seesorb® 703), Tinuvin® Carboprotect, 2-(3,5-di-t-amyl-2-hydroxyphenyl) benzotriazole and 2-(2-hydroxy-5-t-octylphenyl) benzotriazole.

Nowadays, the best compound family for UV and blue cutting through incorporation into an eyeglass substrate are benzotriazoles. However, most of the products available on the market exhibit a maximum absorption wavelength (Amax) below or equal 350 nm, as they have been designed to protect polyolefins C—C bonds from photo-degradation, leading to poor or no absorption at 400 nm and over. Non-chlorinated benzotriazoles show no absorption above 400 nm and thus are not suitable in formulations for cutting blue light. The best benzotriazoles on the market are the chlorinated homologs, such as Seesorb® 703 (2-(2-hydroxy-3-tert-butyl-5-methylphenyl)-5-chlorobenzotriazole) and Eversorb® 109 (2-(2-hydroxy-3-tert-butyl-5-carboxypropylphenyl)-5-chlorobenzotriazole), which have a maximum absortion peak at 350 nm, and Tinuvin® Carboprotect, which has a maximum absortion peak at 375 nm (measurements in ethanol). The latter compound exhibits a satisfactory absorption in the blue light range in solution but has two drawbacks. As it is strongly degraded by peroxide initiators, such as the one contained in the CR-39® formulation, a plastic polymer commonly used in the manufacture of eyeglass lenses, light cutting properties undergo a huge degradation during the transition liquid monomer formulation/polymerized material (blue shift). Therefore, a high amount of benzotriazole absorber is required to obtain the expected light cut off. In addition, degradation products are increasing the yellow index of the polymerized material. Therefore, most of the commercial benzotriazole absorbers are not adapted to ophthalmic use.

Further, incorporating into an optical material composition an optical filtering means able to cut the wavelengths that may be harmful can prove difficult (in particular when it is devoid of cross-linking group), as it is necessary to adapt the formulation of the optical material composition to avoid compatibility issues, in particular with UV absorbers that are prone to precipitation or migration outside the substrate. It is especially difficult to get a transparent material without cosmetic defects such as haze, and the adaptation of the formulation of the optical material composition in order to solubilize the optical filtering means might modify the properties, in particular the mechanical properties, of the final optical material.

In view of the foregoing issues, there is a need for new molecules able to inhibit transmission of UV light and at least part of the phototoxic blue light, that is compatible with the other components of the optical material composition and efficient in low amount to limit the alteration of the mechanical properties of the polymer substrate, and as stable as possible toward radical initiators to limit yellowing. It is also desirable that the optical material exhibits no cosmetic defects. The optical material should be perceived as transparent and mostly colorless by an external observer. The process for manufacturing such an article should be simple, easy to implement and reproducible.

To address the needs of the present invention and to remedy to the mentioned drawbacks of the prior art, the applicant designed and synthesized specific benzotriazole compounds with an optimized electronic contribution of substituents on the molecule core structure. The present invention provides an eyeglass lens comprising a substrate made of an optical material comprising a polymer matrix and at least one 2-(2-hydroxy-5-$R^1$-phenyl)benzotriazole, in which $R^1$ is a resonant group, the optical transmittance through a 2 mm thick layer of said optical material being lower than 1% for each light wavelength ranging from 280 to 405 nm.

The invention provides a substrate-borne UV and blue light filter in a simple way and at competitive cost by using 2-(2-hydroxyphenyl)benzotriazole derivatives bearing a resonant group in position 5 of the hydroxyphenyl ring. This substituent is responsible for a shift to the red end (the high wavelengths side) of the absorption spectrum of the molecule, also called redshift, and leads to an increased absorption in the blue light range. The benzotriazole compounds disclosed herein are significantly more efficient than typical benzotriazole absorbers, can be easily incorporated in polymerizable compositions. The polymerizable compositions containing the UV-absorbers of the invention have good processability characteristics such as machinability, and are suitable as optical plastics.

The foregoing and other objects, features and advantages of the present invention will become readily apparent to those skilled in the art from a reading of the detailed description hereafter when considered in conjunction with the accompanying drawing, wherein.

The term "eyeglass lens" is used to mean a lens adapted to a spectacle frame to protect the eye and/or correct the sight. Said lens may be a lens or lens blank and can be chosen from afocal, unifocal, bifocal, trifocal and progressive lenses. The eyeglass lens according to the invention typically comprises a transparent optical substrate.

In the present description, unless otherwise specified, an optical substrate/material is understood to be transparent when the observation of an image through said optical article is perceived with no significant loss of contrast, that is, when the formation of an image through said optical article is obtained without adversely affecting the quality of the image. This definition of the term "transparent" can be applied to all objects qualified as such in the description, unless otherwise specified.

The eyeglass lens of the present invention may be coated on its front main surface, rear main side, or both sides with one or more functional coatings. As used herein, the rear face of the substrate is intended to mean the face which, when using the article, is the nearest from the wearer's eye. It is generally a concave face. On the contrary, the front face of the substrate is the face which, when using the article, is the most distant from the wearer's eye. It is generally a convex face. The optical article can also be a plano article.

A substrate, in the sense of the present invention, should be understood to mean an uncoated substrate, and generally has two main faces. The substrate may in particular be an optically transparent material having the shape of an optical article, for example an ophthalmic lens destined to be mounted in glasses. In this context, the term "substrate" is understood to mean the base constituent material of the optical lens and more particularly of the ophthalmic lens. This material acts as support for a stack of one or more coatings or layers.

The substrate of the article of the invention is an organic glass substrate, for instance an organic glass made from a thermoplastic or thermosetting plastic, generally chosen from transparent materials of ophthalmic grade used in the ophthalmic industry.

The benzotriazole UV absorbers of the present invention can be incorporated into any thermoplastic and thermoset resins, preferably thermoset resins.

Thermoplastic material may be selected from, for instance: polyamides; polyimide; polysulfones; polycarbonates; polyurethanes; poly(ethylene terephthalate), polymethylmethacrylate (PMMA) and copolymers thereof. Preferred thermoplastic materials are polycarbonates.

The preferred class of substrate materials comprises thermoset resins which may be selected from, for instance: (meth)acrylic or thio(meth)acrylic polymers and copolymers or polyethoxylated aromatic (meth)acrylates, urethane and thiourethane polymers and copolymers, epoxy polymers and copolymers, episulfide polymers and copolymers, resins resulting from polymerization or (co)polymerization of alkylene glycol bis allyl carbonates such as polymers and copolymers of diethylene glycol bis(allylcarbonate) (marketed, for instance, under the trade name CR-39® by the PPG Industries company, the corresponding marketed lenses being referred to as ORMA® lenses from ESSILOR).

The preferred polymer matrixes comprise at least one of a polyurethane, polythiourethane, polyepisulfide, polymer obtained from a polyol allyl carbonate (the preferred polyol being glycol), polycarbonate, or poly(meth)acrylate.

The most preferred substrates are made of thermoset materials, in particular resins resulting from polymerization or (co)polymerization of alkylene glycol bis allyl carbonates such as polymers and copolymers of diethylene glycol bis(allylcarbonate), polythiourethane resins resulting from copolymerization of at least one polyisocyanate and at least one polythiol, such as those having a refractive index of 1.60 or 1.67, or polyepisulfide resins resulting from copolymerization of at least one polyepisulfide and at least one polythiol, such as those having a refractive index of 1.74.

Specific examples of substrates suitable to the present invention are those obtained from thermosetting polythiourethane resins, which are marketed by the Mitsui Toatsu Chemicals company as MR® series, in particular MR6®, MR7® and MR8® resins. These substrates as well as the monomers used for their preparation are especially described in the U.S. Pat. Nos. 4,689,387, 4,775,733, 5,059,673, 5,087,758 and 5,191,055.

The present benzotriazole absorbers are particularly suitable to polymer matrixes comprising at least one polymer obtained from diethylene glycol bis(allyl carbonate) or ethylene glycol bis(allyl carbonate), which inherently filter UV light only up to 365 nm (without any UV absorber), and which cause some commercial benzotriazole absorbers to be degraded during polymerization.

There are no particular restrictions on the method used to manufacture the optical article which includes a substrate made of an optical material according to the invention.

The polymer matrix of the present optical article can be obtained from methods that are well known to those of ordinary skill in the art, typically from an optical material composition ("substrate composition") comprising polymerizable compounds such as monomers, oligomers and/or prepolymers. The preferred polymerizable compounds are allyl glycol carbonates, polythiols, episulfides, polyisocyanates, polyisothiocyanates and (meth)acrylates.

In an embodiment, a combination of diethylene glycol bis(allylcarbonate) and eventually oligomers of diethylene glycol bis(allylcarbonate) is used.

In another embodiment, a combination of a polyisocyanate compound and a polyol compound, a combination of a polyisocyanate compound and a polythiol compound, or a combination of a polyepisulfide compound and a polythiol compound is used. In particular, polyisocyanate compounds may be selected from hexamethylene diisocyanate, xylylene diisocyanate, isophorone diisocyanate, bis(isocyanatomethyl)cyclohexane, dicyclohexylmethane diisocyanate, 2,5(or 2,6)-bis(isocyanatomethyl)bicyclo-[2.2.1]-heptane and mixtures thereof. In particular, polyepisulfide compounds may be selected from bis(2,3-epithiopropyl)sulfide, bis(2,3-epithiopropyl)disulfide and mixtures thereof. In particular, polythiol compounds may be selected from trimethylolpropanetris(2-mercaptoacetate), trimethylolpropanetris(3-mercaptopropionate), trimethylolethanetris(2-mercaptoacetate), trimethylolethanetris(3-mercaptopropionate), pentaerythritoltetrakis(2-mercaptoacetate), pentaerythritoltetrakis(3-mercaptopropionate), bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercaptopropyl)disulfide, 4-mercaptomethyl-1,8-dimercapto-3,6-dithiaoctane, 4,8(or 4,7 or 5,7)-dimercaptomethyl-1,11-dimercapto-3,6,9-trithiaundecane, and mixtures thereof. Preferred embodiments are combination of xylylene diisocyanate and pentaerythritoltetrakis(3-mercaptopropionate); combination of xylylene diisocyanate and 4-mercaptomethyl-1,8-dimercapto-3,6-dithiaoctane; combination of 2,5 (or 2,6)-bis(isocyanatomethyl)bicyclo-[2.2.1]-heptane, pentaerythritoltetrakis(3-mercaptopropionate) and 4-mercaptomethyl-1,8-dimercapto-3,6-dithiaoctane; combination of xylylene diisocyanate and 4,8(or 4,7 or 5,7)-dimercaptomethyl-1,11-dimercapto-3,6,9-trithiaundecane; combination of dicyclohexylmethane diisocyanate and 4,8(or 4,7 or 5,7)-dimercaptomethyl-1,11-dimercapto-3,6,9-trithiaundecane; or a combination of bis(2,3-epithiopropyl)disulfide and 4,8(or 4,7 or 5,7)-dimercaptomethyl-1,11-dimercapto-3,6,9-trithiaundecane.

Examples of useful polymerizable compounds are disclosed e.g. in WO 2014/133111.

The benzotriazole compounds of the present invention can be incorporated into the mass of the substrate by methods well known in the art, preferably during the manufacture of the substrate itself, for example by casting polymerization or injection molding.

This is preferably carried out by mixing the compound in the optical material composition (an optical material resin or a polymerizable composition) and then forming the substrate by curing the (liquid) composition in an appropriate mold.

More specifically, the optical material composition is poured into the cavity of a mold held together using a gasket or tape. Depending on the desired characteristics of the resulting optical material, degassing can be performed under reduced pressure and/or filtration can be performed under increased pressure or reduced pressure before pouring the optical material composition in the mold. After pouring the composition, the casting mold, preferably a lens casting mold, can be heated in an oven or a heating device immersed in water according to a predetermined temperature program to cure the resin in the mold. The resin molded product may be annealed if necessary.

Other methods can also be employed, in particular when the benzotriazole compound is not sufficiently resistant to the high temperatures involved during casting or injection molding. Such methods include impregnation or imbibition methods consisting in dipping the substrate in an organic solvent and/or water based hot bath in which the benzotriazole has been dispersed (which then diffuses in the body of the substrate), the diffusion methods described in JP 2000-314088 and JP 2000-241601, involving an impregnable temporary coating, or contactless coloration using a sublimable material, such as described in U.S. Pat. Nos. 6,534,443 and 6,554,873.

The optical material composition can contain additives commonly used in the art other than those mentioned above, for example internal mold release agents, resin modifiers, light stabilizers, polymerization catalysts, color balancing agents, chain extenders, crosslinking agents, free radical scavengers such as antioxidants, dyes, pigments, fillers, and adhesion accelerators.

The optical material composition according to the invention generally comprises a system for initiating the polymerization (catalyst). The polymerization initiating system can comprise one or more thermal or photochemical polymerization initiating agents or alternatively, a mixture of thermal and photochemical polymerization initiating agents, depending on the nature of the polymerizable compounds. Generally, the initiating agents are used in a proportion of 0.01 to 5% by weight with respect to the total weight of polymerizable compounds present in the composition.

In particular, for substrates resulting from polymerization or (co)polymerization of polyurethane and polythiourethane resins, preferred catalysts are selected from alkyltins, alkyltin oxides, metal coordination complexes or amines, more preferably alkyltins. A preferred proportion for alkyltins is 0.02 to 2% by weight with respect to the total weight of polymerizable compounds present in the composition. Preferred alkyltins are dibutyltin dichloride and dimethyltin dichloride.

Free radical initiators that are typically recommended for use with polyol(allyl carbonate) monomers, such as diethylene glycol bis(allyl carbonate), are diisopropyl peroxydicarbonate (IPP), benzoyl peroxide (BPO) and monoperoxycarbonate initiators, such as tertiarybutylperoxy isopropyl carbonate.

The benzotriazoles according to the invention are 2-(2-hydroxy-5-$R^1$-phenyl)benzotriazoles providing a specific optical transmittance, i.e., compounds of formula (I), in which $R^1$ is a resonant group, the $R^2$ groups are identical or different monovalent groups, n is a integer ranging from 0 to 3, the $R^3$ groups are identical or different monovalent groups, m is a integer ranging from 0 to 4:

(I)

Said benzotriazoles of formula I must be chosen and used in the polymer matrix of an optical material in an amount such that the optical transmittance through a 2 mm thick layer of said optical material is lower than 1% for each light wavelength ranging from 280 to 405 nm, preferably from 280 to 410 nm.

An advantage of the present invention is that concerned molecules are simple to synthesize using synthetic pathways of typical benzotriazole and widespread raw materials, thus making their production cost-competitive.

The benzotriazoles according to the invention preferably have a molecular weight lower than or equal to 500 g/mol, more preferably lower than 475 g/mol, even more preferably lower than 450 g/mol, as benzotriazoles of high molecular weight tend to be less soluble in the polymerizable composition. In this regard, said benzotriazoles preferably have only one 2-(2'-hydroxyphenyl)benzotriazole group per molecule, and more generally only one benzotriazole group per molecule.

The preferred benzotriazoles according to the invention are compounds of formula (I) in which $R^1$ is a resonant group, the $R^2$ groups are identical or different monovalent groups, n is an integer equal to 0 or 1, the $R^3$ groups are identical or different monovalent groups, m is an integer ranging from 0 to 2.

The 2-(2-hydroxy-5-$R^1$-phenyl)benzotriazoles do preferably not comprise any polymerizable group selected from allylic, acrylic and methacrylic moieties. The benzotriazoles according to the invention do preferably not comprise any unsaturated polymerizable group or cross-linking group, such as a non aromatic C=C double bond, which could reticulate the benzotriazole within the substrate during polymerization. In other words, the present benzotriazoles are preferably not polymerizable compounds and are rather physically entrapped in the final material.

$R^1$ is a resonant group, i.e., a group providing resonance to the structure. In other words, $R^1$ has the ability to effect electron distribution through resonance structures.

$R^1$ is in position 5 on the 2-phenyl group of the present benzotriazole compounds, i.e., in para position relative to the hydroxyl group. The best $R^1$ groups are electron donating groups because they have a better ability of shifting to the red end the benzotriazole absorption spectrum, i.e., to the high wavelengths. This red shifting effect results in an optical material having a more significant extinction in the blue-violet region of the visible spectrum (400-450 nm), in other words a higher light cut-off wavelength. The $R^1$ groups are all the more efficient as they have a strong resonance electronic effect. Preferably, $R^1$ has a Hammett resonance constant $\sigma_R$ lower than or equal to −0.22. In another embodiment, $R^1$ has a Hammett constant $\sigma_{para}$ lower than or equal to −0.20, preferably lower than or equal to −0.25.

$R^1$ is preferably selected from the groups amino, hydroxyl, alkoxy, aryloxy, alkylamino, arylamino, dialkylamino, diarylamino, (aryl)(alkyl)amino, formamido, alkylamido, arylamido, alkylimino, and arylimino, more preferably from the groups amino, hydroxyl, alkoxy, aryloxy, alkylamino, arylamino, dialkylamino, diarylamino, and (aryl)(alkyl)amino.

In one embodiment, $R^1$ is a group of formula O—$R^4$, in which $R^4$ is a hydrogen atom or a linear or branched, substituted or unsubstituted alkyl or aryl group, preferably a linear or branched, substituted or unsubstituted alkyl group comprising from 1 to 14 carbon atoms, more preferably from 1 to 10 carbon atoms, still more preferably from 1 to 6 carbon atoms. $R^4$ is preferably a C1-C4 linear or branched alkyl group, such as a methyl, ethyl, propyl or butyl group. In one embodiment, $R^4$ is a cycloalkyl or heterocycloalkyl group having a C5-C7 ring optionally substituted with identical or different groups that may be selected from the same groups as the $R^2$ groups described hereunder, preferably linear or branched alkyl chains comprising from 1 to 6 carbon atoms, linear or branched alkoxy chains comprising from 1 to 6 carbon, hydroxyl groups, and amino groups. $R^4$ is preferably a (non substituted) hydrocarbon group.

In another embodiment, $R^1$ is a group of formula $NR^{4a}R^{4b}$, in which $R^{4a}$ and $R^{4b}$ independently represent groups that may be chosen from the same groups as the $R^4$ groups.

In another embodiment, the benzotriazole compound according to the invention is a 2-(2-hydroxy-5-$R^1$-phenyl) benzotriazole in which $R^1$ is an optionally substituted aryl carbonyl group of formula —C(=O)—Ar (connected through the carbonyl group). Said aryl group Ar is preferably substituted with one or more electron donating groups, preferably two, which are preferably chosen from the groups amino, hydroxyl, alkoxy, aryloxy, alkylamino, arylamino, dialkylamino, diarylamino, (aryl)(alkyl)amino, formamido, alkylamido, arylamido, alkylimino, and arylimino. A preferred aryl carbonyl $R^1$ group is the 2,4-dihydroxyphenyl carbonyl group. A specific example of benzotriazole compound provided with this $R^1$ group is the 2-(2,4-dihydroxy-5-(2,4-dihydroxyphenylcarbonyl) phenyl) benzotriazole (IX).

In the present patent application, the term "alkyl" means a linear or branched, saturated or unsaturated monovalent hydrocarbon-based radical, preferably containing from 1 to 25 carbon atoms. The term alkyl includes acyclic groups preferably containing from 1 to 8 carbon atoms such as methyl, ethyl, n-propyl, isopropyl, butyl and n-hexyl groups, the cycloalkyl groups preferably containing from 3 to 7 carbon atoms, the cycloalkylmethyl groups preferably containing from 4 to 8 carbon atoms.

The term "cycloalkyl" also includes "heterocycloalkyl" groups, i.e. non-aromatic monocyclic or polycyclic rings in which one or more carbon atoms of the ring(s) have been replaced with a heteroatom such as nitrogen, oxygen, phosphorus or sulfur. The heterocycloalkyl group preferably comprises 1 to 4 endocyclic heteroatoms. The heterocycloalkyl groups may be structures containing one or more nonaromatic rings. In the structures bearing several rings, the rings may be fused, covalently linked or linked via a common divalent group such as a methylene, ethylene or carbonyl group. A heterocycloalkyl group can have one or more carbon-carbon double bonds or carbon-heteroatoms double bonds in the ring as long as the ring is not rendered aromatic by their presence. Preferably, the heterocycloalkyl group is a monocyclic or bicyclic ring, more preferably, a monocyclic ring, wherein the ring comprises from 2 to 6 carbon atoms and from 1 to 3 heteroatoms. Illustrative examples of heterocycloalkyl groups include, but are not limited to, aziridinyl, pyrrolidinyl, piperidinyl, piperazinyl, morpholinyl, thiomorpholinyl, thiomorpholino, tetrahydrofuranyl, tetrahydrothiofuranyl, tetrahydropyranyl, and pyranyl.

The term "substituted alkyl" group means an alkyl group as defined above, connected via an $sp^3$ carbon atom and substituted with one or more aryl groups and/or comprising one or more heteroatoms such as N, S or O. Examples that can be mentioned include arylalkyl groups such as the trityl group (—$CPh_3$), the benzyl group or the 4-methoxybenzyl group, alkoxyalkyl groups, especially dialkoxymethyl groups such as diethoxymethyl or dimethoxymethyl groups, $CH_2CO_2R^{11}$ groups, in which $R^{11}$ represents an optionally substituted alkyl or aryl group.

The term "aryl" denotes an aromatic monovalent carbocyclic radical comprising only one ring (for example a phenyl group) or several, optionally fused, rings (for example naphthyl or terphenyl groups), which may optionally be substituted with one or more groups such as, without limitation, alkyl (for example methyl), hydroxyalkyl, aminoalkyl, hydroxyl, thiol, amino, halo (fluoro, bromo, iodo or chloro), nitro, alkylthio, alkoxy (for example methoxy), aryloxy, monoalkylamino, dialkylamino, acyl, carboxyl, alkoxycarbonyl, aryloxycarbonyl, hydroxysulfonyl, alkoxysulfonyl, aryloxysulfonyl, alkylsulfonyl, alkylsulfinyl, cyano, trifluoromethyl, tetrazolyl, carbamoyl, alkylcarbamoyl or dialkylcarbamoyl groups. Alternatively, two adjacent positions of the aromatic ring may be substituted with a methylenedioxy or ethylenedioxy group.

The term "aryl" also includes "heteroaryl" groups, i.e. aromatic rings in which one or more carbon atoms of the aromatic ring(s) have been replaced with a heteroatom such as nitrogen, oxygen, phosphorus or sulfur. The heteroaryl group preferably comprises 1 to 4 endocyclic heteroatoms. The heteroaryl groups may be structures containing one or more aromatic rings, or structures containing one or more aromatic rings coupled with one or more nonaromatic rings. In the structures bearing several rings, the rings may be fused, covalently linked or linked via a common divalent group such as a methylene, ethylene or carbonyl group. Examples of heteroaryl groups are thienyl (2-thienyl, 3-thienyl), pyridyl (2-pyridyl, 3-pyridyl, 4-pyridyl), isoxazolyl, oxazolyl, phthalimidyl, pyrazolyl, indolyl, furanyl, quinolinyl, phenothiazinyl, thiazolyl, (1,2,3)- and (1,2,4)-triazolyl, tetrazolyl, carbazolyl, pyrazinyl, pyridazinyl, pyrimidyl, triazinyl, pyrrolyl, imidazolyl, benzopyranonyl, and benzo-fused analogs thereof. Preferably, a heteroaryl group is a monocyclic ring, wherein the ring comprises 2 to 5 carbon atoms and 1 to 3 heteroatoms.

The $R^2$ and $R^3$ groups represent independently from each other, identical or different monovalent groups, which are preferably selected from a hydrogen atom, saturated or unsaturated, linear or branched, substituted or unsubstituted hydrocarbon (such as alkyl) groups comprising from 1 to 12 carbon atoms, preferably from 2 to 10 carbon atoms, still preferably from 2 to 5 carbon atoms (hydrocarbon groups are connected to the aryl group through a carbon atom), for example arylalkyl groups, and groups such as hydroxyalkyl, aminoalkyl, hydroxyl, thiol, amino, halo (fluoro, bromo, iodo or chloro), nitro, alkylthio, alkoxy, aryloxy, monoalkylamino, dialkylamino, acyl, carboxyl, alkoxycarbonyl, aryloxycarbonyl, hydroxysulfonyl, alkoxysulfonyl, aryloxysulfonyl, alkylsulfonyl, alkylsulfinyl, cyano, trifluoromethyl, tetrazolyl, carbamoyl, alkylcarbamoyl or dialkylcarbamoyl groups.

The $R^2$ groups are preferably identical or different groups chosen from a hydrogen atom and linear or branched, substituted or unsubstituted hydrocarbon groups comprising from 1 to 6 carbon atoms. $R^2$ is preferably an electron donating group.

In one embodiment, the $R^3$ groups are independently selected from a hydrogen atom and linear or branched, substituted or unsubstituted hydrocarbon groups comprising from 1 to 6 carbon atoms.

In another embodiment, $R^3$ is a hydrogen atom or a resonant group, which is preferably selected from halogen, cyano, amino, hydroxyl, mercapto, carboxy, alkylsulfanyl and arylsulfanyl. $R^3$ is preferably a hydrogen atom or an electron withdrawing group. In this embodiment, the $R^3$ group is preferably a halogen atom in position 4 or 5 on the benzotriazole group, more preferably a chloro group. $R^3$ is ideally located in position 5 on the benzotriazole group.

In one embodiment, n=0. In another embodiment, the benzotriazole according to the invention is not substituted in position 5 of the benzotriazole ring. In a preferred embodiment, m=0, which means that there are no substituents on the carbon atoms of the benzotriazole ring. The preferred compounds of formula I are those are those in which n=m=0, in particular those of formulae II and III, in which $R^4$, $R^{4a}$ and $R^{4b}$ independently represent a hydrogen atom or a linear or branched, substituted or unsubstituted alkyl or aryl group such as described above:

(II)

(III)

Specific examples of benzotriazole derivatives according to the invention are 2-(2-hydroxy-5-methoxyphenyl)benzotriazole of formula IV, 2-(2-hydroxy-5-butoxyphenyl)benzotriazole of formula V, and 2-(2-hydroxy-5-amino phenyl)benzotriazole of formula VI:

(IV)

(V)

(VI)

The amount of benzotriazole compounds used in the present invention is an amount sufficient to provide a satisfactory protection from blue light and UV light but not excessive so as to prevent precipitation. The inventive benzotriazole compounds are generally present in an amount ranging from 0.05 to 3% by weight relative to the optical material (the substrate) total weight (or per 100 parts by weight of the polymerizable compounds or relative to the weight of the optical material composition), preferably from 0.1 to 2.5% by weight, more preferably from 0.15 to 2% by weight. Very high amounts of benzotriazole compounds should be avoided as they may prevent the liquid formulation from curing to a solid material.

As the present benzotriazoles have significant absorption above 400 nm and are stable in the presence of initiators such as peroxides, they can be introduced in the monomer formulation in smaller quantity than previously known benzotriazole UV absorbers, making their use mass and cost efficient and minimizing polymer's mechanical properties degradation and plasticization thereof.

The red shifted benzotriazole UV absorbers that may be used in the present invention have the ability to block light having a wavelength shorter than 400 nm, but also have an absorption spectrum extending to visible blue light range of the electromagnetic spectrum (400-500 nm).

Thus, the benzotriazole compounds of the invention are efficient to improve blue light cutting by absorption, even when used in small amounts. The resulting optical material thus provides a high level of retinal cell protection against retinal cell apoptosis or age-related macular degeneration.

The optical material according to the invention preferably blocks or cuts at least 80% of the light having a wavelength ranging from 280 to 380 nm (preferably from 280 to 400 nm, more preferably from 280 to 405 nm, still more preferably from 280 to 410 nm), more preferably at least 90% and still more preferably at least 95%, essentially through absorption by the benzotriazole UV absorber. In most preferred embodiments, at least 96%, 97%, 98%, 99%, 99.5% or 99.9% of light in the 280-380 nm, 280-400 nm, 280-405 nm or 280-410 m ranges is blocked.

In the present application, "blocking X %" of incident light in a specified wavelength range does not necessarily mean that some wavelengths within the range are totally blocked, although this is possible. Rather, "blocking X %" of incident light in a specified wavelength range means that an average of X % of said light within the range is not transmitted.

In addition, light blocking is considered here for an optical material devoid of any coating, especially antireflective coating. It means that light reflected by optical material is not transmitted and considered as blocked.

The light cut-off wavelength of the optical material is preferably higher than or equal to 400 nm, more preferably higher than or equal to 405 nm, and even more preferably higher than or equal to 410 nm. It is preferably lower than 465 nm, more preferably lower than 450 nm. The higher the light cut-off wavelength, the better the blue light cutting properties. In the present disclosure, the light cut-off wavelength is defined as the wavelength below which light transmission becomes lower than 1%. In other words, it is the highest wavelength for which the transmittance is lower than 1%. The light cut-off wavelength increases with the amount of UV absorbers that is used, but its evolution is low and almost asymptotic at high concentrations of these compounds.

In the present description, unless otherwise specified, optical transmittances/transmissions are measured at the center of the optical article for a thickness ranging from 0.7 to 2 mm, preferably 2 mm, at normal incidence. As used herein, optical transmittance within a wavelength range is an average of light transmitted within this range and is not weighted according to the sensitivity of the eye at each wavelength of the range, unless otherwise specified. Last, optical transmittance is measured for optical articles having no coatings, in particular no antireflective coatings. In particular, reflection at both air/substrate interfaces reduces significantly optical transmittance, around 4-5% for each interface, i.e. 8-10% for a lens.

In one embodiment, the optical material is configured such that the optical transmittance of the optical article is satisfying at least one of the characteristics (1) to (3) below and preferably these three characteristics:

(1) the optical transmittance at 400 nm is 1% or less;

(2) the optical transmittance at 420 nm is 60% or less;
(3) the optical transmittance at 440 nm is 80% or more.

Other preferred benzotriazoles according to the invention lead to an optical material having an optical transmittance higher than 65%, more preferably higher than 75%, for light having a wavelength of 430 nm, when incorporated into a 2-mm thick layer of said material.

Further, it may be particularly desirable in some cases to selectively filter a relatively small portion of the blue spectrum, i.e., within the 380-450 nm region. Indeed, it has been found that blocking too much of the blue spectrum can interfere with scotopic vision and mechanisms for regulating biorhythms, referred to as "circadian cycles". Thus, in a preferred embodiment, the optical material blocks less than 1% of light having a wavelength ranging from 465 to 495 nm, preferably from 450 to 550 nm. In this embodiment, the optical material selectively blocks the phototoxic blue light and transmits the blue light implicated in circadian rhythms. Preferably, the optical material transmits at least 85% of light having a wavelength ranging from 465 to 495 nm, more preferably from 450 to 550 nm. In another embodiment, the optical material does not absorb light in the 465-495 nm range, preferably the 450-550 nm range.

The optical material according to the invention preferably has a relative light transmission factor in the visible spectrum Tv higher than or equal to 85%, preferably higher than or equal to 87%, more preferably higher than or equal to 88%, and better higher than or equal to 89%.

Optical articles made from optical material according to the invention can be coated with antireflective coatings on one or both air/substrate interface(s). In such embodiments, Tv factor preferably ranges from 85% to 99%, more preferably from 88% to 98%, even better from 88% to 97%.

The Tv factor, also called "luminous transmission" of the system, is such as defined in the standard NF EN 1836 and relates to an average in the 380-780 nm wavelength range that is weighted according to the sensitivity of the eye at each wavelength of the range and measured under D65 illumination conditions (daylight).

The optical material according to the invention has improved color properties, especially when it is color-balanced, which can be quantified by the yellowness index Yi. The degree of whiteness of the inventive optical material may be quantified by means of colorimetric measurements, based on the CIE tristimulus values X, Y, Z such as described in the standard ASTM E313 with illuminant C observer 2°. Despite the presence of the benzotriazole compound according to the invention in an amount sufficient to cut at least part of the blue light, the optical material according to the invention generally has a low yellowness index Yi, i.e., lower than 10, more preferably lower than 8, even more preferably lower than 5, as measured according to the above standard. The yellowness index Yi is calculated per ASTM method E313 through the relation Yi=(127.69 X−105.92 Z))/Y, where X, Y, and Z are the CIE tristimulus values.

A further advantage of the present ultraviolet-absorbing benzotriazole compounds is that they are compatible with the polymerizable composition and the resulting polymerized material. No precipitation is observed after curing, even at high concentration.

In particular, polymerizable compositions comprising the present ultraviolet-absorbing benzotriazoles and sulfide anti yellowing additives yield polymerized materials with low Yi. Sulfide anti yellowing additives may be selected from dialkyl thiodipropionate, dialkyl thiodiglycolate, thiane, dithiane or trithiane, dialkyl sulfide, dialkyl disulfide, dialkenyl sulfide and dialkenyl disulfide. More particularly, sulfides may be selected from ditridecyl thiodipropionate, diethylhexyl thiodipropionate, dioctyl thiodipropionate, dimethyl thiodipropionate, diethyl thiodiglycolate, and mixtures thereof.

The invention also relates to a method for preparing an optical material, in particular an eyeglass lens, such as herein described, comprising:
  obtaining a polymerizable composition comprising at least one 2-(2-hydroxy-5-$R^1$-phenyl)benzotriazole, in which $R^1$ is a resonant group, and at least one polymerizable compound,
  curing said polymerizable composition, preferably in a mold, so as to form a substrate made of an optical material comprising a polymer matrix and said at least one 2-(2-hydroxy-5-$R^1$-phenyl)benzotriazole,
the optical transmittance through a 2 mm thick layer of said optical material being lower than 1% for each light wavelength ranging from 280 to 405 nm.

In a preferred embodiment, said at least one polymerizable compound is selected from polyol allyl carbonates, polythiols, episulfides, polyisocyanates, polyisothiocyanates and (meth)acrylates. More preferably, the polymer matrix comprises at least one polymer obtained from diethylene glycol bis(allyl carbonate) or ethylene glycol bis(allyl carbonate).

In one embodiment of the invention, the polymerizable composition is prepared by first mixing the monomer(s) with the benzotriazole compound, and additives such as catalysts are then added.

The process according to the invention in advantageous since it requires no specific steps such as tinting and no specific coating comprising UV absorbers.

The following examples illustrate the present invention in a more detailed, but non-limiting manner. Unless stated otherwise, all thicknesses disclosed in the present application relate to physical thicknesses.

EXAMPLES

1. Chemicals Used

Optical materials were prepared from:
  a composition A comprising two polymerizable monomers, diethylene glycol bis(allyl carbonate) (CR-39, CAS No. 142-22-3) and tetraallyl urethane (CR-39E, available from PPG industries), a benzotriazole compound as an UV and optionally blue light absorber, and di-isopropylperoxycarbonate as a catalyst (CAS No. 105-64-6), or
  a composition B comprising three polymerizable monomers: 2,5(or 2,6)-bis(isocyanatomethyl)bicyclo-[2.2.1]-heptane, also known as bisisocyanatonorbonane (ISO, CAS No. 74091-64-8), pentaerythritol tetrakis (3-mercaptopropionate) (THIOL1, CAS No. 7575-23-7), and 4-mercaptomethyl-1,8-dimercapto-3,6-dithiaoctane (THIOL2, CAS No. 131538-00-6), a benzotriazole compound as an UV and optionally blue light absorber, Diaresin blue J as a bluing agent (BA, CAS No. 86090-40-6), and dimethyltin dichloride as a catalyst (CAS No. 753-73-1).

The benzotriazole compounds according to the invention used in the examples were 2-(2-hydroxy-5-methoxyphenyl) benzotriazole (formula IV), 2-(2-hydroxy-5-butoxyphenyl) benzotriazole (formula V), and 2-(2-hydroxy-5-amino phenyl)benzotriazole (formula VI). The structures of these compounds are reminded hereunder:

(IV)

(VI)

(V)

The following comparative benzotriazole compounds were used: Seesorb® 703 (2-(2-hydroxy-3-tert-butyl-5-methylphenyl)-5-chlorobenzotriazole, CAS No. 3896-11-5, formula VII), Tinuvin® Carboprotect (this compound does not fall within the scope of the present invention), and Seesorb® 709 (2-(2-hydroxy-5-tert-octylphenyl) benzotriazole, CAS No. 52188-76-8, formula VIII). Compounds VII and VIII are devoid of resonant group in position 5 of the 2-hydroxyphenyl ring. The structures of Seesorb® 703 (VII) and of Seesorb® 709 (VIII) are reminded hereunder:

(VII)

(VIII)

2. Synthesis of 2-(2-hydroxy-5-$R^1$-phenyl)benzotriazoles ($R^1$ Being a Resonant Group)

a) Synthesis of 2-(2-hydroxy-5-methoxyphenyl)benzotriazole

Step A: Diazonium Salt Preparation 6.91 g (0.05 mol, 1 eq) of o-nitroaniline was crushed and transferred in a 250 mL bottle, followed by 30 mL of hydrochloric acid 37%. The mixture was stirred vigorously, and sonication may be used if needed to disperse remaining sediments to enable a homogeneous mixture. The pale tan to yellow opaque suspension was cooled in an ice bath. When the temperature reached 0-5° C., addition of $NaNO_2$ solution (prepared from 3.61 g of $NaNO_2$—0.052 mol, 1.05 eq—in 10 g distilled water) was started in the stirred chlorhydrate suspension. During addition, the temperature must not exceed 5° C., and should ideally be maintained around 0° C. The diazonium salt solution was filtered on a glass Buchner using cold water and isolated in a pre-cooled filtering flask.

Step B: o-nitrophenylazo Intermediate Preparation 2 g of NaOH were weighed in a beaker, followed by 150 mL of water (a few mL of water were added first to quickly dissolve NaOH), 15 g of $Na_2CO_3$ and 6.21 g of p-methoxyphenol (0.05 mol, 1 eq). The solution was stirred until full dissolution. It was then cooled in an ice bath to 5° C. The diazonium salt solution prepared in step A was slowly added (over 30 min) under mechanical stirring, keeping the temperature below 5° C. A brick-red solid appeared, and the suspension became viscous. The stirring speed was increased to ensure fast dilution of the diazonium salt solution. Once all the diazonium salt was added, the mixture was further stirred for 30 min below 5° C., then filtered under vacuum. The cake was washed with ice cold water until the filtrate was neutral, and dried at 80° C.

Step C: Cyclization of the o-nitrophenylazo Intermediate 7.8 g of NaOH and 115 mL of distilled water were introduced in a two-neck 250 mL round bottom flask fitted with a dropping funned and a condenser. 8.19 g (0.03 mol) of the azo intermediate prepared in step B was added and stirred until dissolution. The dropping funnel was charged with a solution prepared from 14.34 g (0.082 mol, 2.75 eq) of sodium dithionite in 60 g of water. The solution was added dropwise over one hour under vigorous magnetic stirring. A slightly exothermic reaction occurred, and the mixture became dark green at mid addition. Once all the dithionite solution was added, the mixture was stirred at room temperature for one hour, then refluxed for one additional hour. The solution was filtered on a glass Buchner while still warm, then transferred in a 250 mL beaker. Under mechanical mixing, c.a. 4 mL of 30% hydrochloric acid were added portionwise, until pH 7-8 was reached. The suspension was filtered and the porous cake was washed with cold water. The moist cake was triturated in a small amount of acetone, filtered and dried. The material was recrystallized in boiling methanol. Yellow needles were obtained, having a melting point of 124° C. The structure was confirmed by IR and NMR.

b) Synthesis of 2-(2-hydroxy-5-aminophenyl)benzotriazole

This compound was obtained by using essentially the same protocol as above, replacing the p-methoxyphenol by 4-acetamidophenol, maintaining reflux for 4 h during the reductive cyclization step to ensure total deacetylation of the amino group, and by recrystallizing the crude product in an ethanol/water 1/1 V/V mixture. A yellow powder was obtained, having a melting point of 185° C. The structure was confirmed by IR.

c) Synthesis of 2-(2-hydroxy-5-butoxyphenyl)benzotriazole

This compound was obtained by using essentially the same protocol as above, replacing the p-methoxyphenol by 4-butoxyphenol. The structure was confirmed by IR and NMR.

The reaction scheme allowing the preparation of various 2-(2-hydroxy-5-R¹-phenyl)benzotriazoles is shown hereunder:

3. Manufacture of Lenses by Casting

Convex and concave glass plano molds having 71 mm diameter were assembled by using typing process. A center thickness adjustment was made to obtain lenses with 2 mm center thickness.

The formulations of the examples and comparative examples were prepared in small batch size by using a beaker with a glass tube for nitrogen intake and a vacuum connection.

For composition A, the CR-39E® monomer was first added (2 parts by weight), followed by the CR-39® monomer (100–X parts by weight). Then the benzotriazole absorber was added (X parts by weight, X ranging from 0.25 to 1.0), and the beaker content was mixed until full dissolution. The di-isopropylperoxycarbonate catalyst was added (2.92 parts by weight) and the mixture was stirred thoroughly, then degassed and filtered.

The assembled molds were filled with the final formulations using a syringe, and the polymerization reaction was carried out in a regulated electronic oven according to the following cycle: 3 hours at about 45-50° C., regular temperature increase during 11 hours at about 3° C./hour, 3 hours at about 80-90° C. and 2 hours at about 60-70° C.

The molds were then disassembled to obtain lenses comprising a body of a thermoset material. The lenses were cleaned with isopropyl alcohol, then annealed for 1 h at 100° C.

For composition B, the benzotriazole UV absorber component was mixed with the ISO monomer (isocyanate part, 50.6 g) at room temperature (25° C.) until a homogeneous mixture was obtained. The dimethyl tin dichloride catalyst (40 mg) was added in the reaction mixture, which was then cooled down to 10° C. prior to addition of the thiol monomers THIOL1 (23.9 g) and THIOL2 (25.3 g), and stirred under vacuum until homogeneous. The bluing agent (200 mg) was added at the end of the preparation.

The assembled molds were filled with the final formulations using a syringe, and the polymerization reaction was carried out in a regulated electronic oven at maximum 130° C. for 1 day. The molds were then disassembled to obtain lenses comprising a body of a thermoset material. The lenses were cleaned by immersion and sonication in a surfactant solution, then rinsed and dried.

4. Formulations Prepared and Characterizations

The concentrations of the benzotriazole compounds used in the formulations prepared and the characterizations of the final lenses are shown hereunder in table 1 for composition A and table 2 for composition B.

The light cut-off wavelengths were determined from the light transmission spectra, which were recorded from a wearer's view angle using a Cary 4000 spectrophotometer from Hunter, with the back (concave) side of the lens (2 mm thickness at the center) facing the detector and light incoming on the front side of the lens, under D65 illumination conditions (daylight).

Figure 2:
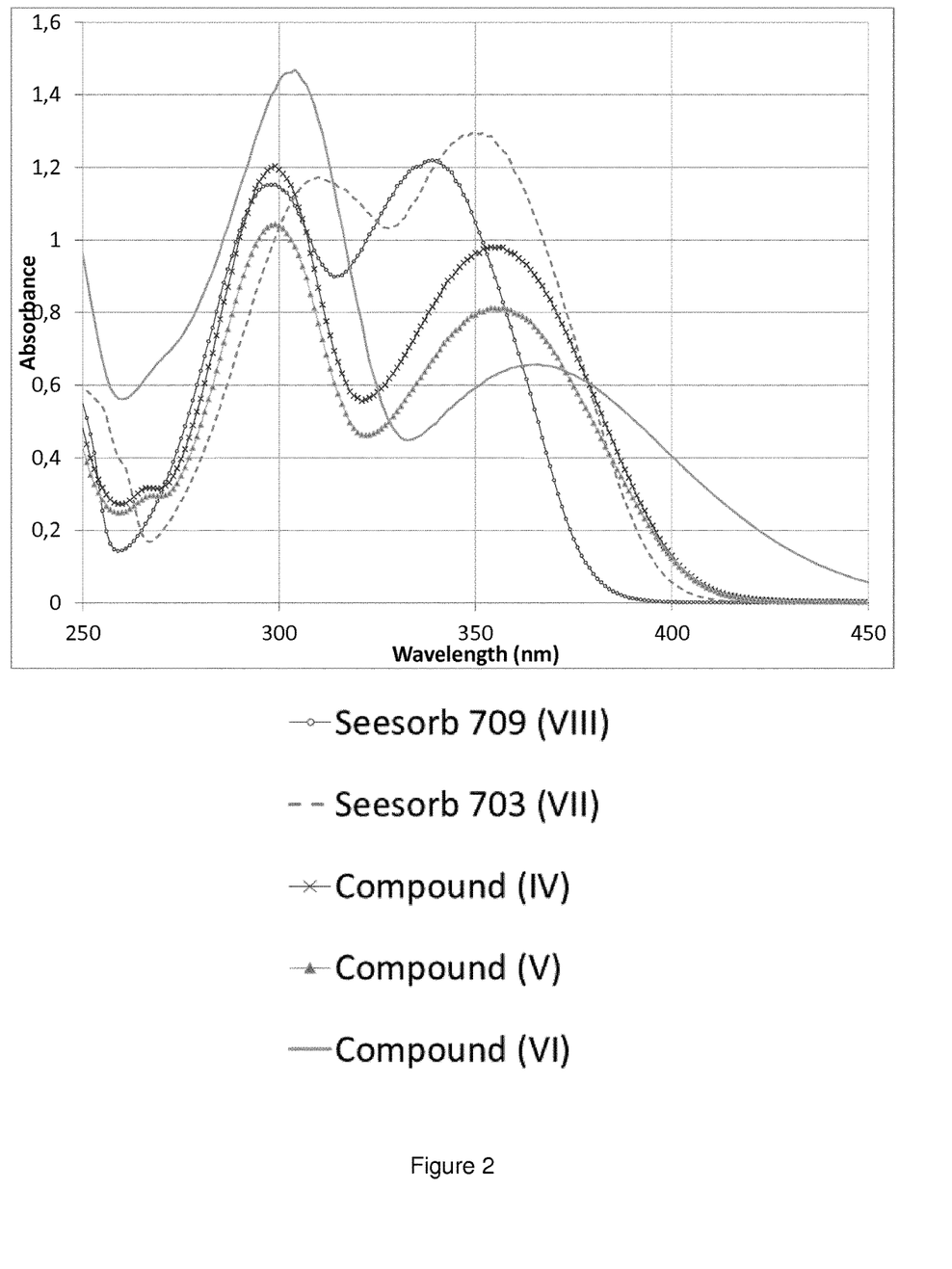

Comparison of inventive compounds of formulae IV, V and VI with comparative compounds shows that the presence of a resonant group in position 5 of the 2-hydroxyphenyl ring provides with a red shifting effect (FIG. 2). Indeed, methyl and tert-octyl substituents are not resonant groups, whereas metoxy and butoxy and amino substituents are resonant groups.

The yellowness index Yi of the prepared lenses was calculated as described above, by measuring on a white background with the above spectrophotometer the CIE tristimulus values X, Y, Z such as described in the standard ASTM E 313-05, through reflection measures, with the front (convex) side of the lens facing the detector and light incoming on said front side. This way of measuring Yi, from an observer's view angle, is the closest to the actual wearing situation.

TABLE 1

| Benzotriazole | Concentration (%) (*) | Light cut-off (nm) | Yi |
|---|---|---|---|
| VII (Seesorb ® 703, comparative) | 0.05 | 369 | 1.7 |
| | 0.1 | 381 | 2.5 |
| | 0.2 | 390 | 3.9 |
| | 0.3 | 394 | 4.9 |
| | 0.4 | 397 | 5.8 |
| | 0.7 | 401 | 9.1 |
| | 1.0 | 404 | 12.5 |
| IV | 0.025 | 367 | 2.1 |
| | 0.05 | 379 | 3.3 |
| | 0.1 | 393 | 5.3 |
| | 0.2 | 402 | 8.9 |
| | 0.3 | 406 | 12.0 |
| | 0.4 | 409 | 13.8 |
| | 0.7 | 414 | 20.3 |
| Tinuvin ® Carboprotect (comparative) | 0.025 | 364 | 3.0 |
| | 0.05 | 373 | 4.7 |
| | 0.1 | 392 | 7.9 |
| | 0.2 | 404 | 12.1 |
| | 0.7 | 417 | 22.2 |

(*) In parts by weight ("X"), for 100 parts by weight of the main monomer (CR-39 ®).

As can be seen, the benzotriazole of formula IV according to the invention offers protection from UV light and interesting blue light cut levels in composition A. It is much more efficient, at iso-weight, than the best red shifted chlorobenzotriazole available on the market, Seesorb® 703, in terms of UV/blue light cutting. Even massive amounts of Seesorb® 703 (1 part by weight) cannot deliver a significant blue cut level (404 nm). The polymer matrix containing such a high amount of absorber is also highly plasticized. Thus, Seesorb® 703 has the drawback of causing a strong plasticization effect at modest UV cut-off wavelength.

In terms of optical properties, the benzotriazole of formula IV according to the invention behaves almost similarly as the most red-shifted benzotriazole on the market, Tinuvin® Carboprotect (same mass efficiency, i.e., in the final lens). Although the latter was more promising than the benzotriazole of formula IV in terms of light cut-off, when considering the absorption spectra of the respective compounds in solution (see FIG. 1, 0.4 mmol/L in ethanol, measurement in quartz tank, 2 mm optical path), Tinuvin® Carboprotect underwent a dramatic decrease in light cut-off wavelength between the solution state and the solid state (final polymerized lens). For example, at a concentration of 0.1 parts by weight of UV absorber for 100 parts by weight of the main monomer (CR-39®), the light cut-off wavelength was reduced from 410 nm (liquid solution) to 392 nm (solid state) for Tinuvin® Carboprotect, from 400 nm (liquid solution) to 393 nm (solid state) for the inventive compound of formula IV, and from 391 nm (liquid solution) to 381 nm (solid state) for Seesorb® 703.

Further, Tinuvin® Carboprotect underwent degradation during the lens polymerization, leading to an increase of the level of yellowness of the lens. Globally, Tinuvin® Carboprotect showed the highest Yi values for any given wavelength. At fixed light cut-off wavelength, the inventive benzotriazole of formula IV has a Yi close to that of Seesorb® 703, and lower than that of Tinuvin® Carboprotect (Yi~9 vs. Yi~12 for a light cut-off wavelength of 402 nm).

TABLE 2

| Benzotriazole | Concentration (%) (*) | Light cut-off (nm) | Yi |
|---|---|---|---|
| VII (Seesorb ® 703, comparative) | 0.5 | 410 | 7.3 |
| | 0.75 | 412 | 9.3 |
| | 1.0 | 414 | 10 |
| | 1.5 | 416 | 17.8 |
| | 2.0 | 417.5 | 16.5 |
| IV | 0.1 | 401 | 6.2 |
| | 0.2 | 408 | 9.5 |
| | 0.3 | 412 | 12.2 |
| | 0.4 | 414 | 14.3 |
| | 0.5 | 416 | 16 |

(*) In parts by weight relative to the weight of composition B.

Similar results were obtained in composition B with benzotriazole of formula IV according to the invention. It is much more efficient, at iso-weight, than compound VII (Seesorb® 703), in terms of UV/blue light cutting. Even if yellowness index is slightly increased, the use of a lower amount of additive provides lenses with better mechanical properties.

Figure 1:
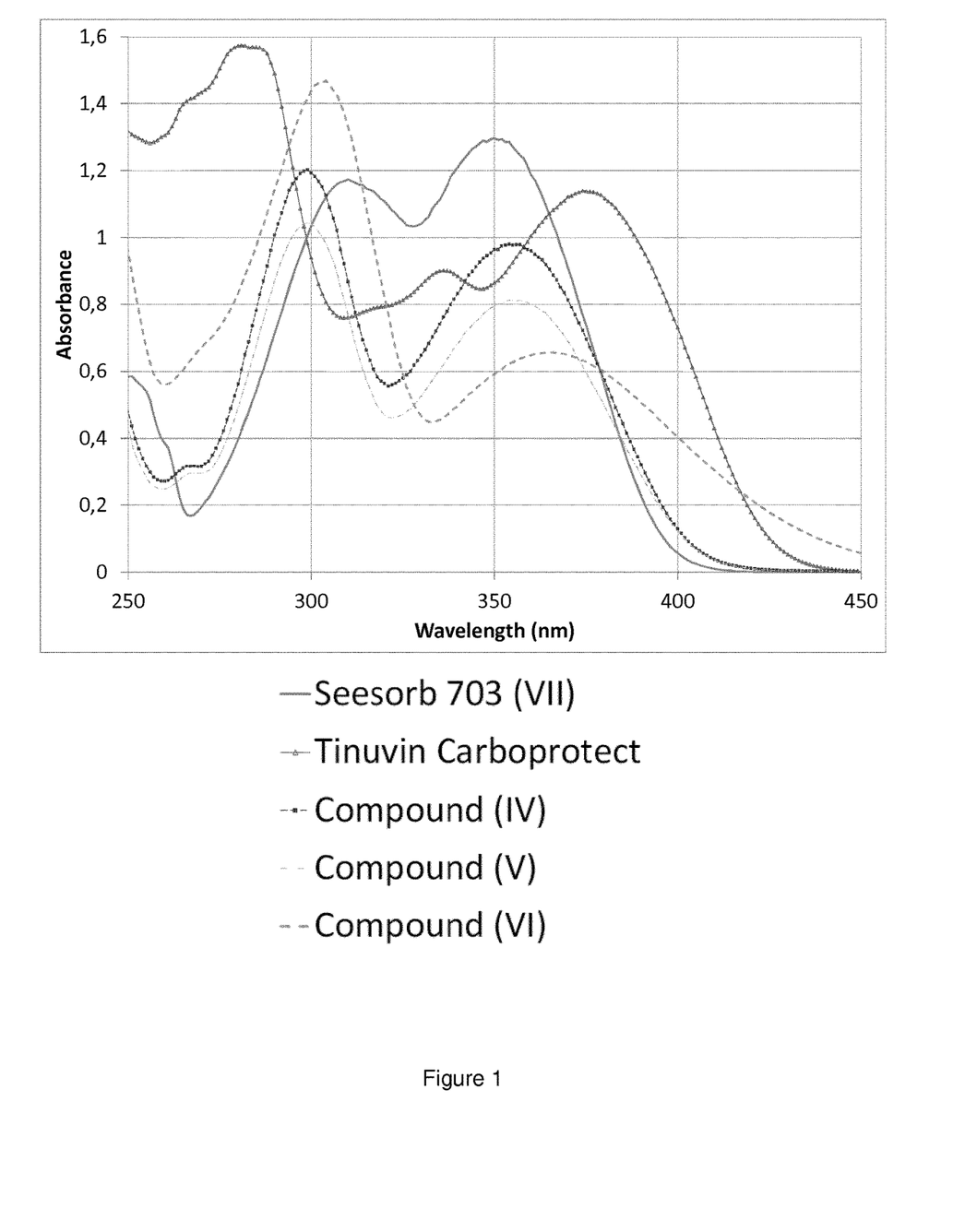
FIGS. 1 and 2 represent the absorption spectrum of various benzotriazoles according to the invention and comparative benzotriazoles between 250 and 450 nm.

FIGS. 1 and 2 also show that the inventive benzotriazole of formula VI is able to absorb at much higher wavelengths than Tinuvin® Carboprotect and comparative compounds of formulae VII and VIII.

It has also been checked that the mechanical properties of a lens substrate comprising the inventive benzotriazole of formula IV were much higher than those of a lens substrate comprising the same weight of Seesorb® 703.

The invention claimed is:

1. An eyeglass lens comprising a substrate made of an optical material comprising a polymer matrix and at least one 2-(2-hydroxy-5-$R^1$-phenyl)benzotriazole, in which $F^1$ is a resonant group, wherein optical transmittance through a 2 mm thick layer of said optical material is lower than 1% for each light wavelength ranging from 280 to 405 nm.

2. The eyeglass lens of claim 1, wherein said at least one 2-(2-hydroxy-5-$R^1$-phenyl)benzotriazole does not comprise any polymerizable group selected from allylic, acrylic and methacrylic moieties.

3. The eyeglass lens of claim 1, wherein said benzotriazole is a compound of formula (I):

in which $R^1$ is a resonant group, the $R^2$ groups are identical or different monovalent groups, n is an integer equal to 0 or 1, the $R^3$ groups are identical or different monovalent groups, m is an integer ranging from 0 to 2.

4. The eyeglass lens of claim 3, wherein m=0.

5. The eyeglass lens of claim 1, wherein $R^1$ is selected from the groups amino, hydroxyl, alkoxy, aryloxy, alkylamino, arylamino, dialkylamino, diarylamino, (aryl)(alkyl) amino, formamido, alkylamido, arylamido, formyloxy, alkylcarboxy, arylcarboxy, alkylimino, and arylimino.

6. The eyeglass lens of claim 5, wherein $R^1$ is selected from the groups amino, hydroxyl, alkoxy, aryloxy, alkylamino, arylamino, dialkylamino, diarylamino, and (aryl)(alkyl)amino.

7. The eyeglass lens of claim 1, wherein the $R^1$ and $R^3$ groups are independently selected from a hydrogen atom and linear or branched, substituted or unsubstituted hydrocarbon groups comprising from 1 to 6 carbon atoms.

8. The eyeglass lens of claim 1, wherein 2-(2-hydroxy-5-$R^1$-phenyl)benzotriazole, in which $R^1$ is a resonant group, are present in an amount ranging from 0.05 to 3.0% by weight relative to the total weight of the substrate.

9. The eyeglass lens of claim 1, wherein the polymer matrix comprises at least one of a polyurethane, polythiourethane, polyepisulfide, polymer obtained from a polyol allyl carbonate, polycarbonate, or poly(meth)acrylate.

10. The eyeglass lens of claim 9, wherein the polymer matrix comprises at least one polymer obtained from diethylene glycol bis(allyl carbonate) or ethylene glycol bis(allyl carbonate).

11. The eyeglass lens of claim 9, wherein the polymer matrix comprises at least one polymer obtained from copolymerization of at least one polyisocyanate and at least one polythiol or from copolymerization of at least one polyepisulfide and at least one polythiol.

12. The eyeglass lens of claim 1, wherein the optical transmittance through a 2 mm thick layer of said optical material is lower than 1% for each light wavelength ranging from 280 to 410 nm.

13. A method for preparing an eyeglass lens of claim 1, comprising:

obtaining a polymerizable composition comprising at least one 2-(2-hydroxy-5-$R^1$-phenyl)benzotriazole, in which $R^1$ is a resonant group, and at least one polymerizable compound; and curing said polymerizable composition so as to form a substrate made of an optical material comprising a polymer matrix and said at least one 2-(2-hydroxy-5-$R^1$-phenyl)benzotriazole;

wherein the optical transmittance through a 2 mm thick layer of said optical material is lower than 1% for each light wavelength ranging from 280 to 405 nm.

14. The method of claim 13, wherein said at least one polymerizable compound is selected from polyol allyl carbonates, polythiols, episulfides, polyisocyanates, polyisothiocyanates and (meth)acrylates.

15. The method of claim 14, wherein the polymer matrix comprises at least one polymer obtained from diethylene glycol bis(allyl carbonate), ethylene glycol bis(allyl carbonate), from at least one polyisocyanate and at least one polythiol or from at least one polyepisulfide and at least one polythiol.

* * * * *

UNITED STATES PATENT AND TRADEMARK OFFICE
CERTIFICATE OF CORRECTION

PATENT NO.         : 10,838,111 B2                              Page 1 of 1
APPLICATION NO.    : 16/095556
DATED              : November 17, 2020
INVENTOR(S)        : Pierre Fromentin It is certified that error appears in the above-identified patent and that said Letters Patent is hereby corrected as shown below:

In the Claims

<u>Claim 1, Column 20, Line 4:</u>
Delete "which $F^1$ is" and replace with -- which $R^1$ is --.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*